US010159546B2

(12) United States Patent
Kopelman et al.

(10) Patent No.: US 10,159,546 B2
(45) Date of Patent: *Dec. 25, 2018

(54) SYSTEM AND METHOD FOR SCANNING AN INTRAORAL CAVITY

(71) Applicant: ALIGN TECHNOLOGY, INC., San Jose, CA (US)

(72) Inventors: Avi Kopelman, Palo Alto, CA (US); Eldad Taub, Reut (IL); Noam Babayoff, Rishon le Zion (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,297

(22) Filed: Apr. 14, 2017

(65) Prior Publication Data

US 2017/0215998 A1 Aug. 3, 2017

Related U.S. Application Data

(63) Continuation of application No. 12/980,587, filed on Dec. 29, 2010, now Pat. No. 9,683,835, which is a
(Continued)

(51) Int. Cl.
*A61C 9/00* (2006.01)
*A61C 7/00* (2006.01)
(Continued)

(52) U.S. Cl.
CPC .......... *A61C 9/0066* (2013.01); *A61B 5/1077* (2013.01); *A61B 5/4547* (2013.01);
(Continued)

(58) Field of Classification Search
CPC . A61B 5/1077; A61B 5/4547; A61C 13/0004; A61C 9/006
See application file for complete search history.

(56) References Cited

U.S. PATENT DOCUMENTS

| 2,467,432 A | 4/1949 | Kesling |
| 3,407,500 A | 10/1968 | Kesling |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23,1980, Los Angeles, CA, p. 195.
(Continued)

*Primary Examiner* — John Breene
*Assistant Examiner* — Yaritza H Perez Bermudez
(74) *Attorney, Agent, or Firm* — Wilson Sonsini Goodrich & Rosati

(57) ABSTRACT

According to the invention, a method and system are provided for scanning, and for facilitating scanning of, an intraoral cavity. The target parts of the intraoral cavity that it is desired to have scanned are identified, and the spatial s relationships between a scanning device and the target parts of the intraoral cavity suitable for enabling said target parts to be scanned by said scanning device, are also identified or otherwise determined. These relationships are then displayed, and the displayed relationships are used as a guide for scanning the intraoral cavity.

20 Claims, 9 Drawing Sheets

Related U.S. Application Data continuation of application No. 11/889,002, filed on Aug. 8, 2007, now Pat. No. 7,890,290, which is a continuation of application No. 11/365,589, filed on Mar. 2, 2006, now Pat. No. 7,286,954.

(60) Provisional application No. 60/657,705, filed on Mar. 3, 2005.

(51) Int. Cl.
*G06F 19/00* (2018.01)
*A61C 5/77* (2017.01)
*G01B 11/24* (2006.01)
*A61B 5/107* (2006.01)
*A61C 13/00* (2006.01)
*A61B 5/00* (2006.01)
*G16H 50/50* (2018.01)

(52) U.S. Cl.
CPC ............... *A61B 5/743* (2013.01); *A61C 5/77* (2017.02); *A61C 7/002* (2013.01); *A61C 9/006* (2013.01); *A61C 9/008* (2013.01); *A61C 13/0004* (2013.01); *G01B 11/24* (2013.01); *G06F 19/00* (2013.01); *G16H 50/50* (2018.01)

(56) References Cited

U.S. PATENT DOCUMENTS

| | | |
|---|---|---|
| 3,600,808 A | 8/1971 | Reeve |
| 3,660,900 A | 5/1972 | Lawrence |
| 3,683,502 A | 8/1972 | Melvin |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A * | 6/1989 | Brandestini ............ A61C 9/006 433/29 |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,138 A | 6/1991 | Gandrud |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |

(56) References Cited

U.S. PATENT DOCUMENTS

| | | | |
|---|---|---|---|
| 6,044,309 | A | 3/2000 | Honda |
| 6,049,743 | A | 4/2000 | Baba |
| 6,062,861 | A | 5/2000 | Andersson |
| 6,068,482 | A | 5/2000 | Snow |
| 6,099,314 | A | 8/2000 | Kopelman et al. |
| 6,123,544 | A | 9/2000 | Cleary |
| 6,152,731 | A | 11/2000 | Jordan et al. |
| 6,179,611 | B1 | 1/2001 | Everett et al. |
| 6,183,248 | B1 | 2/2001 | Chishti et al. |
| 6,190,165 | B1 | 2/2001 | Andreiko et al. |
| 6,217,325 | B1 | 4/2001 | Chishti et al. |
| 6,217,334 | B1 | 4/2001 | Hultgren |
| 6,244,861 | B1 | 6/2001 | Andreiko et al. |
| 6,309,215 | B1 | 10/2001 | Phan et al. |
| 6,315,553 | B1 | 11/2001 | Sachdeva et al. |
| 6,318,995 | B1 | 11/2001 | Sachdeva et al. |
| 6,322,359 | B1 | 11/2001 | Jordan et al. |
| 6,334,772 | B1 | 1/2002 | Taub et al. |
| 6,350,120 | B1 | 2/2002 | Sachdeva et al. |
| 6,382,975 | B1 | 5/2002 | Poirier |
| 6,398,548 | B1 | 6/2002 | Muhammad et al. |
| 6,402,707 | B1 | 6/2002 | Ernst |
| 6,482,298 | B1 | 11/2002 | Bhatnagar |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,592,371 | B2 | 7/2003 | Durbin et al. |
| 6,594,539 | B1 | 7/2003 | Geng |
| 6,629,840 | B2 | 10/2003 | Chishti et al. |
| 6,648,640 | B2 | 11/2003 | Rubbert et al. |
| 6,664,986 | B1 | 12/2003 | Kopelman et al. |
| 6,697,164 | B1 | 2/2004 | Babayoff et al. |
| 6,705,863 | B2 | 3/2004 | Phan et al. |
| 6,722,880 | B2 | 4/2004 | Chishti et al. |
| 6,882,894 | B2 | 4/2005 | Durbin et al. |
| 7,536,234 | B2 | 5/2009 | Kopelman et al. |
| 8,013,853 | B1 | 9/2011 | Douglas et al. |
| 9,683,835 | B2 | 6/2017 | Kopelman et al. |
| 2002/0006597 | A1 | 1/2002 | Andreiko et al. |
| 2003/0009252 | A1 | 1/2003 | Pavlovskaia et al. |
| 2003/0035107 | A1* | 2/2003 | Overbeck .......... A61B 1/00052 356/405 |
| 2003/0068079 | A1 | 4/2003 | Park |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2005/0186540 | A1* | 8/2005 | Taub .................. A61C 13/0004 433/223 |
| 2006/0154198 | A1* | 7/2006 | Durbin ..................... A61C 9/00 433/29 |
| 2011/0105894 | A1 | 5/2011 | Kopelman et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1434028 A1 | 6/2004 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | S6323656 A | 1/1988 |
| JP | H0428359 A | 1/1992 |
| JP | H08508174 A | 9/1996 |
| JP | 2004081842 A | 3/2004 |
| JP | 2004202069 A | 7/2004 |
| JP | 2004344260 A | 12/2004 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |
| WO | WO-0134057 A1 | 5/2001 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures, " AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

(56) References Cited

OTHER PUBLICATIONS

Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the lnvisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121- 133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 the Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98-Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstress-putonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).

(56) References Cited

OTHER PUBLICATIONS

JCO Interviews, Craig Andreiko, DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984). KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).

(56) References Cited

OTHER PUBLICATIONS

Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).

\* cited by examiner

SYSTEM AND METHOD FOR SCANNING AN INTRAORAL CAVITY

CROSS-REFERENCE

This application is a continuation application of U.S. application Ser. No. 12/980,587, filed Dec. 29, 2010, now U.S. Pat. No. 9,683,835, which is a continuation of U.S. application Ser. No. 11/889,002, filed Aug. 8, 2007, now U.S. Pat. No. 7,890,290, which is a continuation of U.S. application Ser. No. 11/365,589, filed Mar. 2, 2006, now U.S. Pat. No. 7,286,954, which claims the benefit of U.S. Provisional Application No. 60/657,705, filed Mar. 3, 2005, all of which are incorporated herein by reference in their entirety and to which applications we claim priority under 35 USC § 120.

FIELD OF THE INVENTION

This invention relates to a system and method for providing guidance for scanning the intra oral cavity to provide three dimensional data that may be subsequently used in prosthodontic and orthodontic procedures in the intra oral cavity. In particular, the invention relates to such systems and methods that are computerized.

BACKGROUND OF THE INVENTION

In prosthodontic procedures designed to implant a dental prosthesis in the intra oral cavity, the dental site at which the prosthesis is to be implanted in many cases needs to be measured accurately and studied carefully, so that a prosthesis such as a crown or bridge, for example, can be properly designed and dimensioned to fit in place. A good fit is of the highest importance to enable mechanical stresses to be properly transmitted between the prosthesis and the jaw, and to prevent infection of the gums and so on via the interface between the prosthesis and the dental site, for example.

In the prior art, the dental site is prepared by the dental practitioner, and a positive physical model of the site is constructed using known methods. Alternatively, the dental site may be scanned to provide 3D data of the site. In either case, the virtual or real model of the site is sent to the dental lab, which manufactures the prosthesis based on the model. However, if the model is deficient or undefined in certain areas, or if the preparation was not optimally configured for receiving the prosthesis, the dental technician has a more difficult job ahead than otherwise, and the design of the prosthesis may be less than optimal. For example, if the insertion path implied by the preparation for a closely-fitting coping would result in the prosthesis colliding with adjacent teeth, the coping geometry has to be altered to avoid the collision, but this may result in the coping design being less optimal. Further, if the area of the preparation containing the finish line lacks definition, it may not be possible to properly determine the finish line an thus the lower edge of the coping may not be properly designed. Indeed, in some circumstances, the model is rejected and the dental practitioner must re-scan the dental site, or must rework the preparation, so that a suitable prosthesis may be produced.

In orthodontic procedures it is also necessary to provide a model of one or both jaws. Where such orthodontic procedures are designed virtually (herein also referred to as "numerically"), a virtual model of the intraoral cavity is also required, and this may be obtained, inter alia, by scanning the intraoral cavity directly, or by producing a physical model of the dentition, and then scanning the model with a suitable scanner.

Thus, in both prosthodontic and orthodontic procedures, obtaining a three-dimensional (3D) model of a least a part of the intraoral cavity is an initial requirement. When the 3D model is a virtual model, the more complete and accurate the scans of the intraoral cavity are, the higher the quality of the virtual model, and thus the greater the ability to design an optimal prosthesis or orthodontic treatment.

Prior art methods of scanning the intraoral cavity do not provide guidance to the dental practitioner on how to ensure full and accurate scanning of parts of the cavity of interest for a particular orthodontic or prosthodontic procedure. Rather, the dental practitioner uses his or her judgment on site, and it is often the case that the scans of some areas of interest may be defective, while other unimportant areas may be scanned to great accuracy with details, which is wasteful of the practitioner's and the patient's time.

SUMMARY OF THE INVENTION

Herein, "dental material" refers to any material associated with dental structures of the intra oral cavity, including but not limited to natural dental materials such as for example enamel, dentine, pulp, dental roots, and non-natural dental materials such as for example metallic and non-metallic filings, restorations, crowns, bridges, copings, preparations, and so on.

Herein, "dental clinic" refers to the interface between a dental practitioner and a patent, and thus includes any physical entity, in particular a clinic, in which there is interaction between a dental patient and a dental practitioner. While "dental practitioner" typically refers to a dentist, doctor or dental technician, it also includes herein all other caregivers that may interact with a dental patient during the course of a dental treatment. While "dental patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, and any other artificial partial or complete denture.

While the term "preparation" typically refers to the stump (including the finish line and optionally the shoulder) that is left of the tooth that is to be replaced by the prosthesis—typically a crown—and on which the crown is to be mounted, the term herein also includes artificial stumps, pivots, cores and posts, or other devices that may be implanted in the intraoral cavity in such a position or in a position that is optimal for implanting the crown.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "orthodontic procedure" refers, inter alia, to any procedure involving the intraoral cavity and directed to the design, manufacture or installation of orthodontic elements at a dental site within the intraoral cavity, or a real or virtual model thereof, or directed to the design and preparation of the dental site to receive such orthodontic elements.

The term "numerical entity" is used herein synonymously with virtual model, 3D model, and other such terms, and relates to a virtual representation in a computer environment of a real object, typically a dentition or at least a part of intraoral cavity, or of a real model thereof, for example.

The term "scanning" and its analogues refer to any procedure directed at obtaining 3D topographic data of a surface, particularly of a dental surface, and thus includes mechanical methods, typically based on 3D probes for example, optical methods, including for example confocal methods, for example as disclosed in WO 00/08415, the contents of which are incorporated herein in their entirety by reference, or indeed any other method.

The term "display" and its analogues refer to any means or method for delivering a presentation, which may include any information, data, images, sounds, etc, and thus the delivery may be in visual and/or audio form.

The present invention is directed to a method for scanning an intraoral cavity, and thus to a corresponding method for facilitating scanning of an intraoral cavity, the method comprising (a) identifying target parts of the intraoral cavity that it is desired to have scanned;

(b) identifying spatial relationships between a scanning device and said target parts of the intraoral cavity suitable for enabling said target parts to be scanned by said scanning device;

(c) displaying said relationships; and (d) using said displayed relationships as a guide for scanning the intraoral cavity.

The method further comprises the step of scanning said intraoral cavity in a manner substantially conforming to said relationships.

The scanning substantially provides 3D data of said target parts for use in a predetermined procedure. Step (a) may include identifying ancillary parts in said intraoral cavity associated with said target parts, wherein 3D data of said ancillary parts is also required for use in said predetermined dental procedure. Step (b) may comprise, for each said target part and each said ancillary part, determining for said scanning device a series of spatial parameters, each comprising a scanning station data sufficient for enabling said scanner to fully scan said corresponding target part or ancillary part. Optionally, the scanning station data of said series include a proximity and a relative orientation of said scanner with respect to said target part or ancillary part such as to enable said scanner to obtain 3D topographical data of an area of said target part or ancillary part. The series provide 3D topographical data for a corresponding plurality of said areas, wherein said spatial parameters of said series are determined such at least some adjacent said areas overlap one another.

In one embodiment, step (c) comprises displaying a nominal image comprising an image of at least a portion of an nominal intraoral cavity, comprising corresponding said target parts and said ancillary parts, and an image of a nominal scanner in a spatial relationship with respect to one another corresponding to the spatial relationship as determined in step (b) for at least one parameter of said series of parameters. A series of said nominal images may be provided, each image in said series corresponding to a different one of said parameters of said series of parameters. The series of images can be displayed in any predetermined sequence. Optionally, the nominal image comprises 3D attributes. The image may comprise said nominal intraoral cavity at any desired orientation with respect to a predetermined coordinate system. The coordinate system may comprise, for example, an orthogonal Cartesian axes system. The orientation may optionally correspond to a real life view of the intraoral cavity of a patient from the vantage point of a dental practitioner. Optionally, an audio and/or visual cue is provided for prompting the user to proceed to the next image.

In another embodiment, step (c) comprises displaying indicia on a viewfinder capable of providing a video image of the field of view of said scanner, said indicia being indicative of a desired position for associating a predetermined portion of said target parts or ancillary parts in a particular manner with respect therewith. The indicia may comprise, for example, an "+" or an "X" or any other suitable symbol, which may be, for example, geometrical, alphanumeric and so on.

In a variation of this embodiment, the indicia comprise a symbol representative of a profile corresponding to an expected view of said target part or ancillary part in said viewfinder. Optical or image recognition methods can be applied to said video image for providing a profile of the image, said symbol comprising said profile. For example, the profile comprises a shaped line shaped as an outline of a tooth as seen via said viewfinder. The symbol may comprise a shaped line shaped as an outline of a tooth seen in any one of top view, buccal view or lingual view, for example.

Optionally, a series of indicia are provided, each indicia in said series corresponding to a different one of said parameters of said series of parameters. Said series of indicia may be displayed in a predetermined sequence, a next indicia being displayed after the intraoral cavity has been scanned according to the previous said parameter and corresponding indicia. Said next indicia may be displayed together with the immediately preceding indicia. Optionally, indicia relating to different said parameters may be displayed in different colors one from another.

The aforesaid procedure may be, for example, a prosthodontic procedure for a crown with respect to a preparation, said target parts comprising said preparation, and said ancillary parts comprising at least a portion of the teeth adjacent to said preparation and facing said preparation from the opposed jaw.

The aforesaid procedure may be, for example, a procedure is a prosthodontic procedure for a bridge with respect to a plurality of preparations, said target parts comprising said preparations, and said ancillary parts comprising at least a portion of the teeth adjacent to a furthermost distal preparation and adjacent a furthermost mesial preparation, and at least a portion of the teeth facing said preparations from the opposed jaw.

The aforesaid procedure may be, for example, a procedure is an orthodontic procedure, and said target parts comprise the full dentition of at least one jaw of said intraoral cavity. Typically the method of the invention is a computerized method, i.e., executed partly or fully with the aid of a processing unit such as a computer. Nevertheless, at least some embodiments may be executed without the need of a computer.

The present invention also relates to a computer readable medium that embodies in a tangible manner a program executable for guiding the scanning of the intraoral cavity of a patient, comprising:

(a) a first set of data representative of target parts of the intraoral cavity that it is desired to have scanned;

(b) a second set of data representative of spatial relationships between a scanning device arid said target parts of the intraoral cavity suitable for enabling said target parts to be scanned by said scanning device.

The computer readable medium may further comprise means such as manipulation routines, computer instructions, and so on, for example, for manipulating said second set of data for enabling displaying said second data.

The medium may comprise any one of optical discs, magnetic discs, magnetic tapes, and so on, for example.

The present invention is also directed to a system for guiding the scanning of an intraoral cavity, comprising:

(A) input module for identifying target parts of the intraoral cavity that it is desired to have scanned;

(B) processing module for generating spatial relationships between a scanning device and said target parts of the intraoral cavity suitable for enabling said target parts to be scanned by said scanning device;

(C) display module for displaying said relationships.

The system preferably also comprises a suitable scanner for scanning according to said relationships

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In order to understand the invention and to see how it may be carried out in practice, a number of embodiments will now be described, by way of non-limiting example only, with reference to the accompanying drawings, in which.

DETAILED DESCRIPTION OF THE INVENTION

Figure 1:
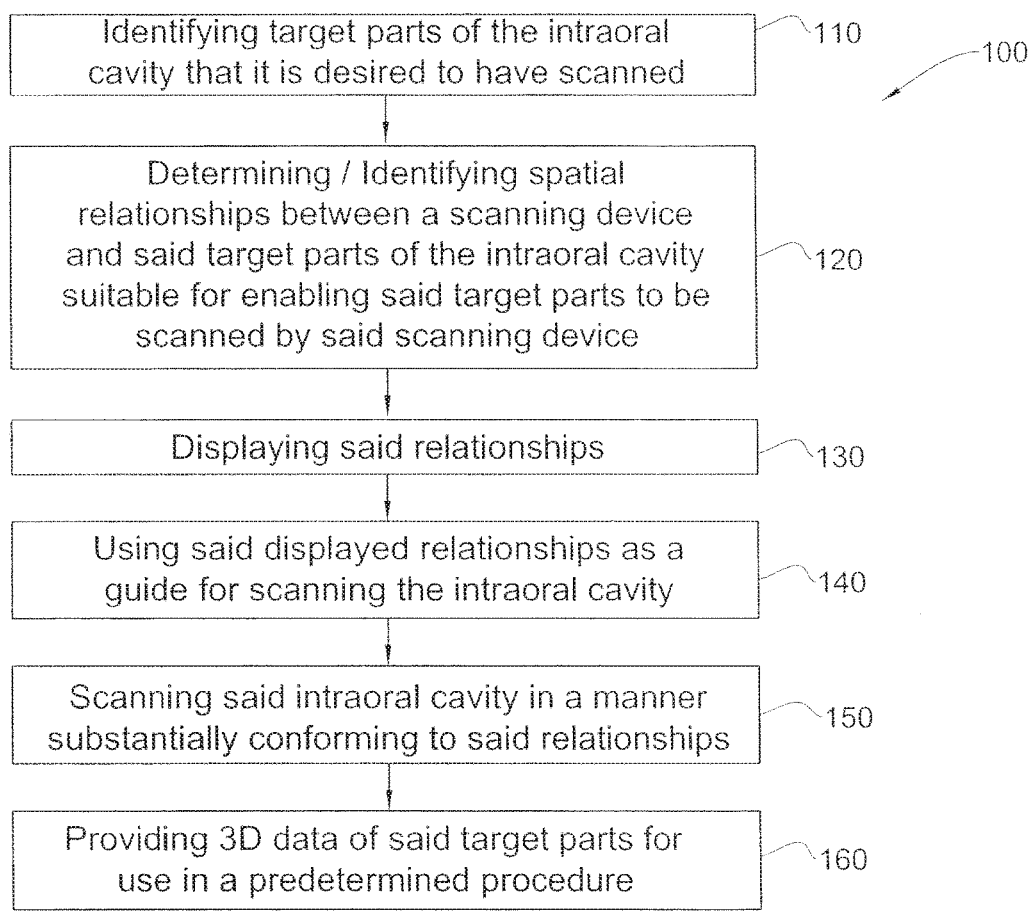
FIG. 1 shows a block diagram of a scanning process according to an embodiment of the invention.
Figure 2:
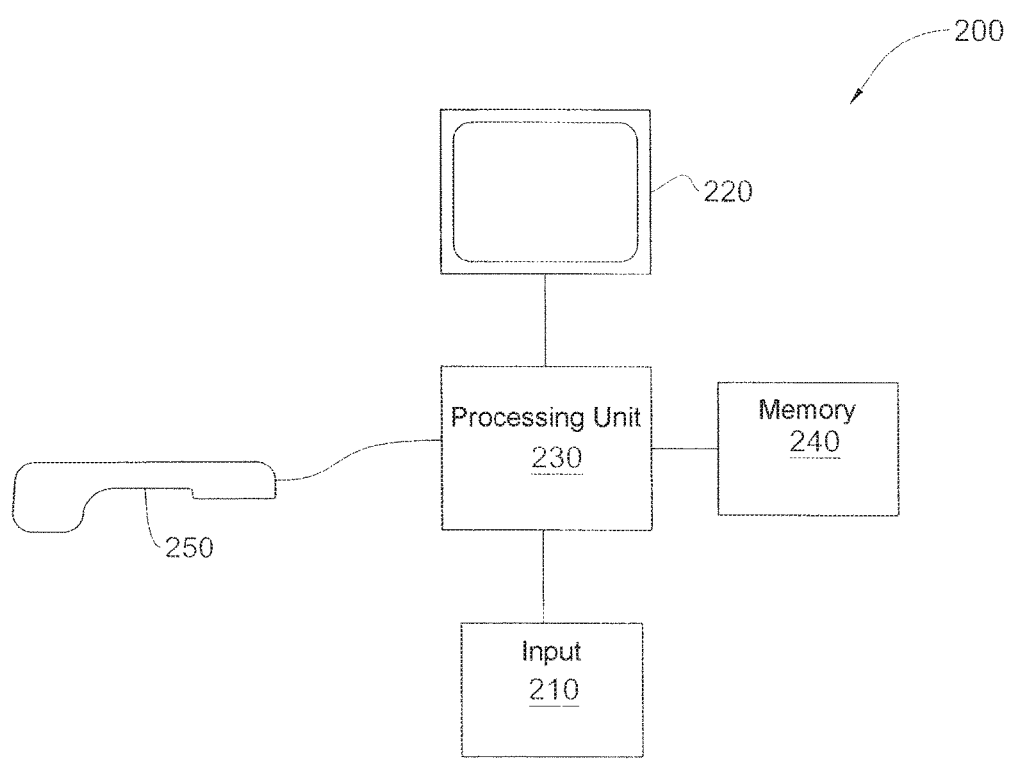
FIG. 2 shows a block diagram of a scanning system according to an embodiment of the invention.

FIG. 1 illustrates a block diagram of the 3D data acquisition process 100 according to an embodiment of the invention, and FIG. 2 illustrates the main elements of a system 200 for carrying out the method according to an embodiment of the invention. The system 200 typically comprises a microprocessor or any other suitable computer, having an input interface or module 210 such as a keyboard, mouse, tablet, and so on, an output device or display means or module 220, typically a screen or monitor but may additionally or alternatively include a printer, or any other display system, a processing unit or module 230 such as for example a CPU, and a memory 240. In some embodiments, a suitable scanner 250 for obtaining 3D data of the intraoral cavity is also operatively connected to the system 200 and interacts therewith, while in other embodiments the scanner 250 may provide the 3D data to another system not necessarily connected in any way with system 200. Advantageously, a probe for determining three dimensional structure by confocal focusing of an array of light beams may be used, for example as manufactured under the name of CB-CAD or as disclosed in WO 00/08415, the contents of which are incorporated herein in their entirety. Alternatively, scanning of the dental cavity to provide the 3D data may be accomplished using any suitable apparatus typically comprising a hand held probe.

Figure 3:
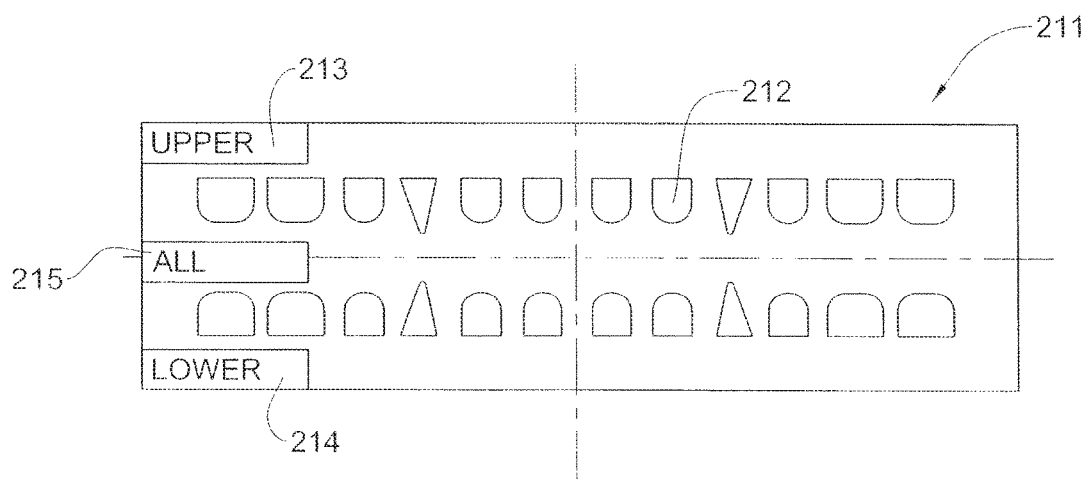
FIG. 3 shows a virtual representation of a dentition enabling target areas to be chosen interactively.

At step 110, the target parts of the intraoral cavity are identified. The target parts are the parts (also referred to herein as zones or areas) of the intraoral cavity which form the focus of a particular dental procedure for a particular patient and regarding which it is desired to obtain the 3D topographical or surface data thereof. The target parts typically include the part of the tooth or the teeth, or other dental material on which the particular procedure is to be performed, and in some cases may include the full mandibular or maxillary arches, or both arches. For example, the procedure may be a prosthodontic procedure involving a crown prosthesis to be designed and fabricated for fitting onto a preparation at a particular dental site. In such a case, the dental practitioner inputs into processing unit 230 the tooth which has been targeted for the procedure, identified according to any suitable convention. For example, and referring to FIG. 3, the display 220 may be used to display a standard image or graphical representation 211 of a nominal intraoral cavity, either with three dimensional (3D) attributes or a simple two dimensional (2D) representation. Alternatively, though, a non-graphical (for example alphanumeric) representation of the intraoral cavity may be provided. Thus, and referring to the example illustrated in FIG. 3, the representation 211 includes a plurality of icons or images or symbols 212, one each corresponding to the teeth in a normal adult or child (the age of the patient having first been input to the processing unit 230). The tooth which is to be the target of the procedure may be identified by "clicking" with the aid of a mouse, for example, on the appropriate symbol 212. Alternatively, any other interactive method may be used for choosing the target tooth, for example by means of a touch screen arrangement. In another example, the identity of the target tooth may be manually input to the processing unit 230 using any conventional nomenclature, a unique coding convention, by selection on a drop-down menu or the like, or in any other suitable manner, the processing unit 230 having been suitably programmed to recognise the choice made by the user.

Alternatively, for a prosthodontics procedure involving a bridge, the two or more teeth that are to be worked on to provide preparations to receive the bridge are identified, for example in a similar to that described above, mutatis mutandis. For orthodontic procedures typically all of the teeth in one or both jaws are required. In such a case, all of the teeth of the upper jaw, lower jaw or both jaws may be chosen by means on a single appropriate symbol, for example as indicated at 213, 214, 215, respectively, in FIG. 3.

The manner in which the intraoral cavity needs to be scanned may depend on the procedure to be applied thereto, as will become clearer as the descriptions proceeds. Thus, the dental practitioner also inputs to the processing unit 230 the identity of the actual procedure. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, the processing unit 230 having been suitably programmed to recognise the choice made by the user. By way of non-limiting example, the procedures may be broadly divided into prosthodontic and orthodontic procedures, and then further subdivided into specific forms of these procedures, as known in the art.

The type of scanner 250 to be used is also input to the processing unit, typically by choosing one among a plurality of options. If the scanner that is being used is not recognisable by the processing unit 230, it may nevertheless be possible to input operating parameters of the scanner thereto instead. For example, the optimal spacing between the scanner head and the tooth surface can be provided, as well as the capture area (and shape thereof) of the dental surface capable of being scanned at this distance. Alternatively, other suitable scanning parameters may be provided. In any case, it may be desired that the virtual model of the dentition, provided using the scanners, may be dimensionally related to the real dentition in a known manner, so that dimensional measurements of the virtual model may be made.

In the next step 120, the processing unit 230 identifies the required spatial relationships that are required for scanning the appropriate parts of the intraoral cavity so that complete and accurate 3D data may be obtained for the procedure in question. This step utilises the data already provided in step 110 for 30 establishing the optimal manner for scanning the intraoral cavity, and thus will depend on the nature of the aforesaid data. Further, according to the method of the invention, additional or ancillary parts of the intraoral cavity that need to be scanned for the particular procedure are also identified, and the spatial relationship between the scanner and these parts are identified or determined. Having identified the target parts and ancillary parts, a scanning protocol is identified or determined by relating the type of scanner, resolution thereof, capture area at an optimal spacing between the scanner head and the dental surface to the target parts and the ancillary parts, either separately or together. The scanning protocol typically comprises a series of scanning stations spatially associated with the dental surfaces of the target part and the ancillary part. Preferably, significant overlapping of the images or scans capable of being obtained at adjacent scanning stations is designed into the scanning protocol to enable good registration, and the 3D data obtained at each scanning station is stitched together to provide a composite 3D virtual model, as is known in the art. A number of examples will now be described.

Figure 4:
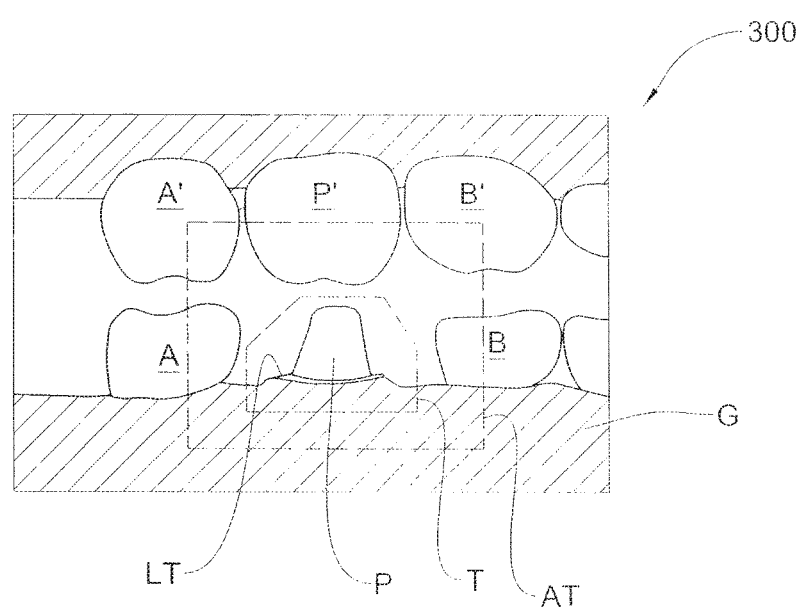
FIG. 4 illustrates target parts and ancillary parts of an intraoral cavity associated with a crown prosthodontic procedure.

FIG. 4 illustrates an idealised portion 300 of the intraoral cavity of a patient requiring a crown prosthesis on a preparation P having teeth A, B, adjacent thereto, and teeth A', P' and B' in opposed relationship thereto from the other jaw. This idealised portion 300 is typically a 3D virtual model of an idealised full dentition of an adult that is stored in the memory 240 of the system 200. By idealised is simply meant that the idealised dentition comprises 3D models of all of the teeth of an adult in their normal relative positions, the 3D models typically being standardised according to the statistical norm regarding size, shape and so on as commonly found in the population. Of course, for the purpose of the invention, any 3D virtual model may be suitable, so long as it includes the 3D virtual models of the teeth corresponding to the teeth of the patient in the required target part and ancillary part. The memory 240 may also comprise idealised virtual models of the teeth of children or of special population groups, and thus the user typically specifies (and may optionally be prompted to 30 do so by the system 200) the age of the patient, or other attribute that best decides the closest idealised virtual model with respect thereto. The memory 240 also comprises, for each virtual tooth model of the 3D virtual model 300, an idealized virtual preparation model, and according to the prosthodontics procedure required by the patient, one or more of the virtual teeth may be replaced with the corresponding one or more virtual preparations.

The target area or part to be scanned is represented by the dotted line T, and includes the preparation P, including the finish line LT, and part of the original tooth above the gumline. When the target area is scanned very accurately, it is possible for the internal surface of a corresponding coping or prosthesis to be accurately designed. Ancillary parts of the intraoral cavity are included in dotted line AT, and comprise parts of the adjacent and opposed teeth, principally teeth A, B, P', and often to a lesser extent teeth A' and B' or parts thereof. Typically, but not necessarily, the resolution of the scanned data for the ancillary parts AT may be less than for the target part T, since the manufacturing accuracy for the external surfaces of the crown prosthesis (the design of which is dependent on the dental surfaces of the ancillary parts) may be substantially less than for the internal surface of the coping or prosthesis. According to the specific nature or properties of the scanner, including the resolution thereof, capture area at an optimal spacing between the scanner head and the dental surface to the target parts and the ancillary parts, the scanning protocol may be designed as follows.

Figure 5:
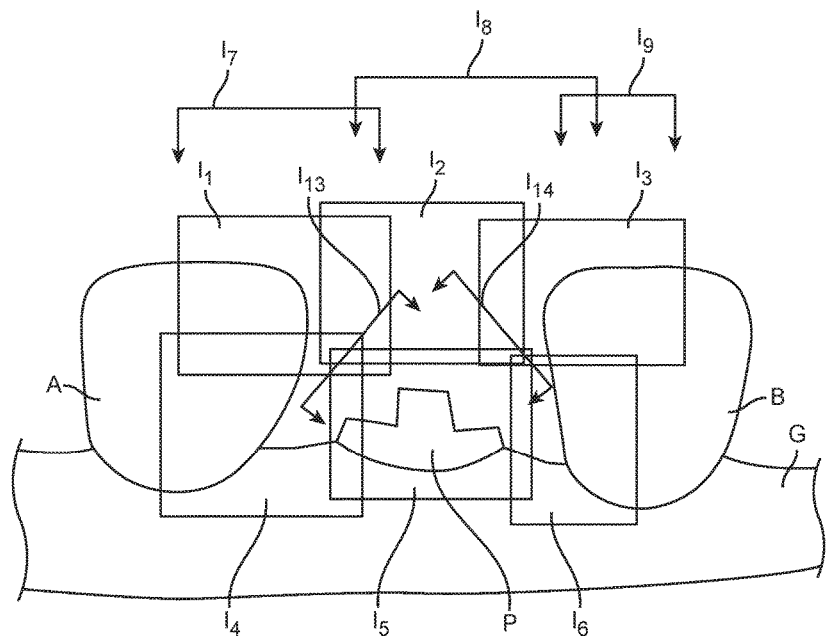
FIG. 5 shows a buccal view of an idealised virtual model of a nominal intraoral cavity showing a plurality of scanning stations.
Figure 6:
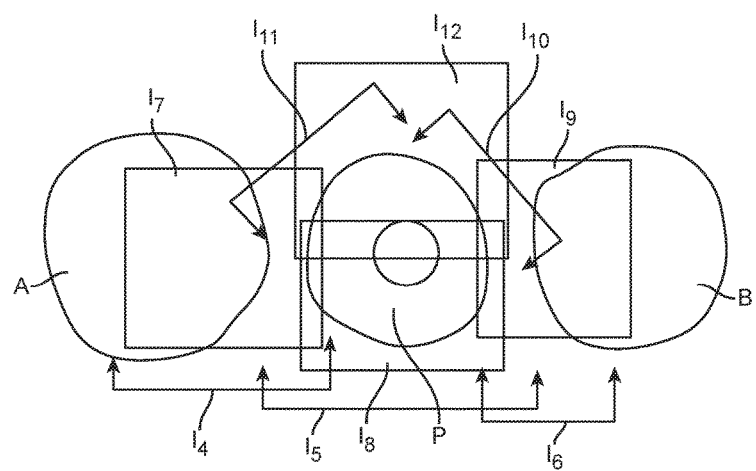
FIG. 6 shows a top view of an idealised virtual model of a nominal intraoral cavity showing a plurality of scanning stations.
Figure 7:
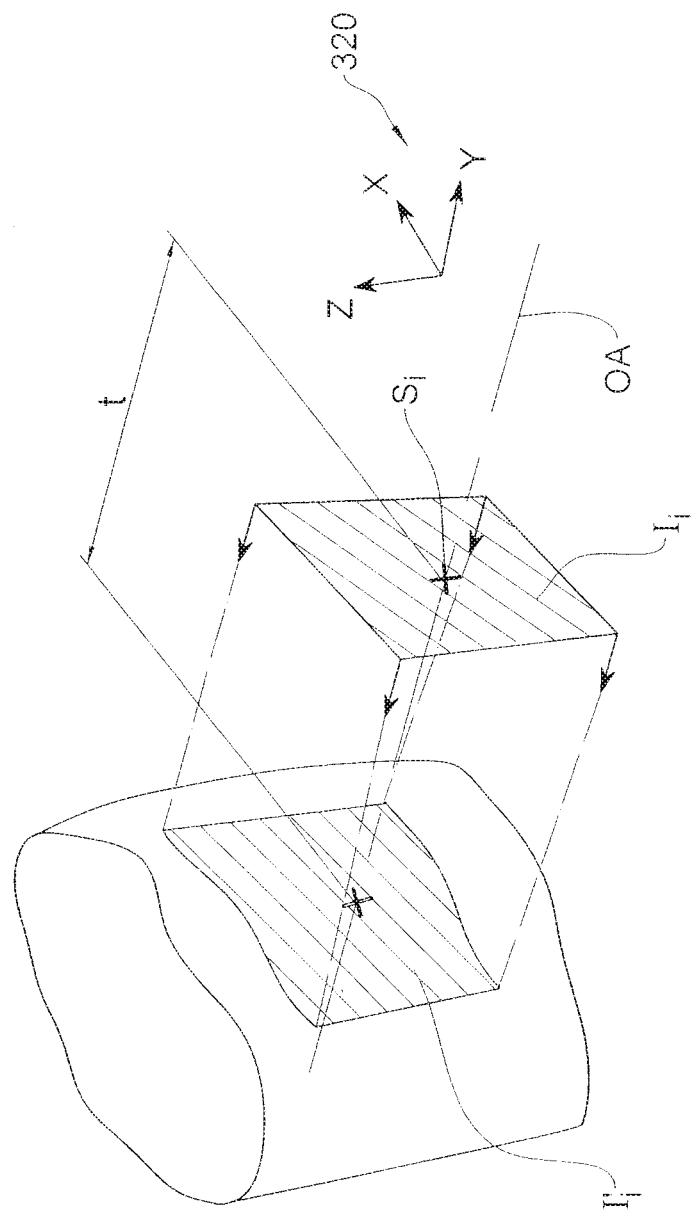
FIG. 7 shows the relationship between an scanning station and a dental surface being scanned thereat.

Referring to FIG. 7, for example, at each scanning station $S_i$ (also referred to herein as an image capture station), 3D data within an area $I_i'$ of the dental surface X of a tooth or preparation, for example, may be captured by the scanner 250, and this area may be represented at the scanning station $S_i$ by a projection $I_i$ of area $I_i'$ on a plane orthogonal to the scanning axis OA of the scanner, and displaced from the dental surface by a dimension t. This dimension t is typically the optimal spacing of the particular scanner with respect to the dental surface X for providing a scan area equivalent to $I_i$ but may be any other suitable spacing. The shape of the area $I_i$ will generally depend on the scanner, and is herein represented by a rectangle. The orientation of the scanning axis OA can be related to a reference coordinate system, for example orthogonal Cartesian axes 320 defined with respect to the model 300, and which are typically easily identified in the real intraoral cavity. Referring to FIGS. 5 and 6, the processing unit 230 determines a plurality of scanning stations $S_i$ surrounding the target part T and the ancillary part AT (referring also to FIG. 4) such that the corresponding areas $I_i'$, in which 3D data is obtained, together cover the full extent of the dental surfaces of interest therein (wherein i=1, 2, 3, . . . 10, 11, 12, 13, 14 . . . ). For example, in FIG. 5, areas $I_1$, $I_2$, $I_3$ and areas $I_4$, $I_5$, $I_6$ represent two sets of three overlapping zones each at approximately two different heights with respect to the gum G which may be sufficient to define a buccal portion of the target part T and the ancillary part AT of the lower jaw of FIG. 4. Similar areas may be required form the lingual side. In FIG. 6, areas $I_4$, $I_5$, $I_6$ are represented by U-shaped symbols, wherein the arms of the U represent the direction along which the scan is taken, i.e., the spatial position of the scanning axis OA of the scanner, and the middle portion of the U represents the corresponding projection $I_i$ as seen edge-on. Thus, exemplary additional areas $I_{10}$ and $I_{11}$ represent additional scanning stations not $I_7$, $I_8$, $I_9$, $I_{12}$, $I_{13}$, $I_{14}$, in FIGS. 5 and $I_{ii}$ represent additional scanning stations not coplanar with the scans at areas $I_4$, $I_5$, $I_6$. Similarly, the areas $I_7$, $I_8$, $I_9$, $I_{12}$, $I_{13}$, $I_{14}$, in FIGS. 5 and 6 represent additional scanning areas taken from above the tooth, with greater overlap between areas being provided in the vicinity of the target part T. For example, areas $I_{13}$, $I_{14}$, being more face-on with respect to parts of the finish line may provide greater accuracy thereof. The location and orientation of scanning stations $S_i$ are determined such that the areas $I_i'$ of the idealised model corresponding to these stations adequately cover the corresponding target parts T and ancillary parts AT thereof. Thus, by reproducing these locations and orientations of the scanner 250 with respect to the real intraoral cavity, the required 3D data of the target part T and ancillary part AT may be obtained, as will be described in greater detail hereinbelow.

The scanning protocol for the dental surfaces of the opposed jaw that are included in the target part T and the ancillary part AT may be obtained in a similar manner to that described above for the lower jaw, mutatis mutandis.

Typically, the scanning protocol will differ when different scanners are used for the same target area, depending on the capture characteristics of the scanner used. Thus, a scanner capable of scanning a larger dental area with each scan (e.g., having a larger field of view) will require less scanning stations to be defined in the scanning protocol than a scanner that is only capable of capturing 3D data of a relatively smaller dental surface. Similarly, the number and disposition of scanning stations for a scanner having a rectangular scanning grid (and thus providing projected scanning areas $I_i$ in the form of corresponding rectangles) will typically be different from those for a scanner having a circular or triangular scanning grid (which would provide projected scanning areas $I_i$ in the form of corresponding circles or triangles, respectively).

In another example (not illustrated) relating to a prosthodontics procedure for a bridge having a single or a plurality of poetics, there are generally two target parts, relating to one or the other of the two preparations on which the bridge is to be anchored, and the ancillary parts to be scanned include at least part of the teeth adjacent to the furthermost distal preparation and adjacent the furthermost mesial preparation, and at least a portion of the teeth facing the preparations from the opposed jaw.

In another example (not illustrated) relating to a prosthodontics procedure requiring a restoration on the buccal or lingual part of a particular tooth, only this target part may need to be scanned in the patient together with the occlusal surfaces of the some of the teeth of the opposite jaw as ancillary parts.

In yet another example (not illustrated) relating to an orthodontic procedure for one or both jaws, the target part may comprise the full dentition of one or both jaws, respectively.

According to the invention, the system 200 may calculate each time a 30 new idealised scanning protocol based on the parameters of the scanner, the procedure, the dental site of the procedure, age of the patent, and so on, and as applied to the idealised virtual model 300.

Alternatively, all the necessary scanning protocols are previously calculated for every type of scanner, procedure, age group and so on, and stored in memory 240, the most suitable protocol being retrieved therefrom when identified according to the particular patient/procedure/scanner parameters that are provided. In this case, the virtual model 300 may not be needed for the purpose of determining customised scanning protocols. Thus, it is possible to provide all the necessary guidance for a particular procedure in printed form, a printed book or pamphlet, for example, by means of a movie or video clip, or in any other communication medium, wherein the user would search for the appropriate guidance images or the like according to the particular parameters of the patient in question, via an index or the like for example, and then open the book/movie and so on at the relevant pages/scene etc., to obtain the guidance required.

Alternatively, the memory 240 comprises a standard scanning protocol for each different type of procedure, and this protocol is modified by the processing unit 230 to take account of at least one of the parameters including: age of dental patient, dental target part, scanner characteristics, and so on.

In step 130, the spatial relationship between the scanning stations $S_i$ and the intraoral cavity are displayed, so that in step 140 these displayed relationships may be used as a guide by the dental practitioner for scanning the intraoral cavity in a manner suitable for obtaining 3D data appropriate for the particular procedure being considered There are many ways of displaying the aforesaid spatial relationships, sonic examples of which will now be described.

Figure 8A:
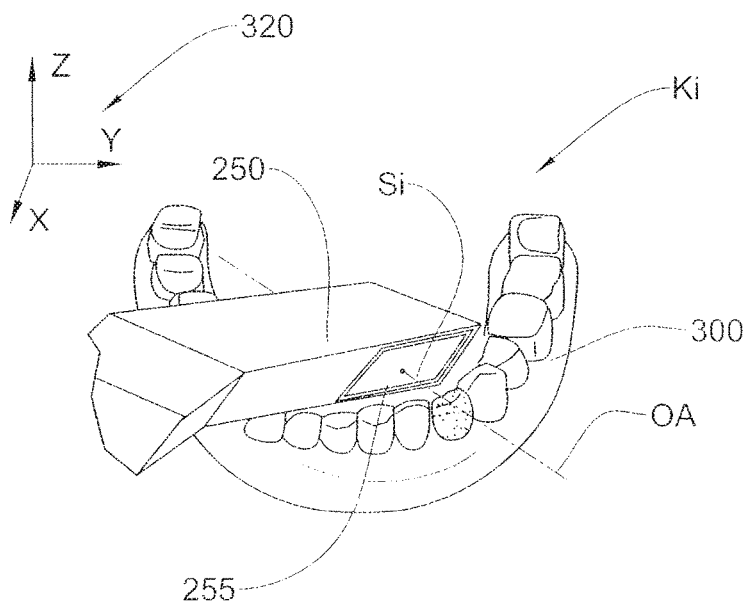
FIGS. 8a and 8b illustrate examples of display output using the system of FIG. 2 according to one embodiment.
Figure 8B:
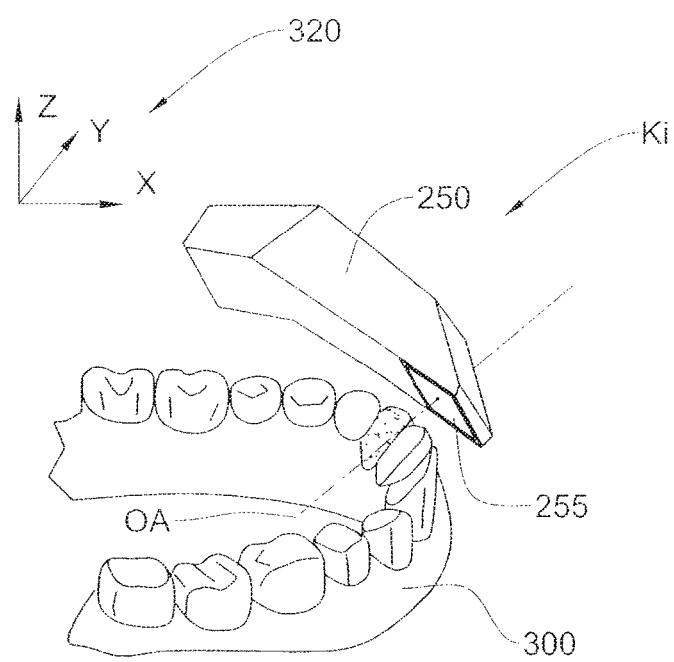

Referring to FIGS. 8a and 8b, for example, a pair of perspective view images $K_i$ may be displayed, on a screen 220 or as printed material, for example, corresponding to the spatial relationship of the scanner 250 with respect to the idealised intraoral cavity 300 at a particular scanning station $S_i$. Additionally or alternatively, a plurality of images showing the relationship at any other desired vantage point (viewpoint) may be provided, including for example the vantage point as would be seen by a dental practitioner with respect to a real intraoral cavity, either by default or by being chosen by the user by interacting with processing unit 230. Optionally, a dynamic image may be provided, in which the user can change the vantage point of the image interactively, in a manner known in the art. Alternatively, a video clip or the like may be provided for providing the user with a sequence of operations of the scanner etc.

Images $K_i$ may be composites of virtual models of the scanner 250 and of the intraoral cavity 300 (typically the aforesaid idealised virtual model) stored in memory 240. These virtual models are manipulated by the processing unit 230 to provide the correct spatial relationship, in virtual space, according to the particular scanning station $S_i$ previously determined, and can be displayed as two dimensional images in a manner known in the art. Optionally, the position of the scanning station $S_i$ and the direction of the scanning axis OA can be displayed with respect to the intraoral cavity 300, additionally or alternatively to the scanner. The scanning axis OA is typically defined as orthogonal to the scanning face 255 of the scanner, but may be defined according to any other preknown suitable geometric or other parameter of the scanner. The images $K_i$ can optionally comprise a representation of the coordinate system, for example orthogonal axes 320, in the orientation appropriate to the vantage point being viewed.

For the purpose of images $K_i$, it may be possible to display the image of the dental surfaces as having 3D attributes and realistic dental morphologies, for example as illustrated in FIGS. 8a and 8b, or alternatively, each dental surface may be represented, for example, by a geometrical form—for example simple wedges representing incisors, cones representing canines, and cylinders representing molars. Optionally, a summary composite image may be first provided (not shown) illustrating the full protocol, for example as a plurality of symbols (e.g. indicia such as "X" or "+", or frames representing the projected areas $I_i$, and so on) may be superposed over one or more images of the idealised dentition—for example, in a manner similar to that illustrated in FIGS. 5 and 6.

Further optionally, the idealised virtual model appearing in images $K_i$ may be custom-modified to show a virtual preparation at each corresponding dental site where a real preparation is to be found, and also virtual teeth may be removed from the model where none are to be found in the real intraoral cavity—for example where teeth have been removed for accommodating a pontic. These features can further facilitate identification of the positions and orientations of the scanner at each of the scanning stations $S_i$.

Further optionally, non-image data may be provided identifying the position and orientation of the scanner at each scanning station $S_i$, and this data may be provided, for example, in the form of a table listing suitable corresponding geometric data, and also including, for example the spacing between the scanner scanning face 255 and the dental surface of interest, an identification of the particular surface being scanned, and so on. Alternatively, the relationships in step 130 may be displayed in alphanumeric form, as a set of instructions or statements describing the relative positions of the scanner and teeth, for example. Alternatively, the relationships in step 130 may be displayed in audible form, wherein for example such instructions or statements are broadcast by a speaker or the like, either from a prerecording, or synthetically created by the system 200.

Further optionally, the scanning stations $S_i$ may be successively displayed in any desired order, for example in an order such as to minimise displacement of the scanner between each successive scan. In this embodiment of step 130 is followed by the step 140 of using the displayed relationships as a scanning guide, and step 150 of scanning the intraoral cavity in a manner substantially conforming to said relationships. To facilitate the dental practitioner's work, the images corresponding to a next scanning station are, optionally, not displayed until the practitioner is confident that he/she has properly scanned the intraoral cavity as required by the current scanning station. This may be accomplished by operatively connecting the scanner 250 to the processing unit 230, and prompting the user whether to display the next scanning station every time a scan is taken (and which is detected by the unit 230). Alternatively, it may be possible, after each scan, to display a video image as taken by the scanner with an idealised 2D virtual image of the idealised virtual model as seen from the vantage point of the scanner for this scanning station, and the user can compare the two images and decide whether or not the particular scan is likely to have sufficiently conformed with the desired relationship.

Figure 9B:
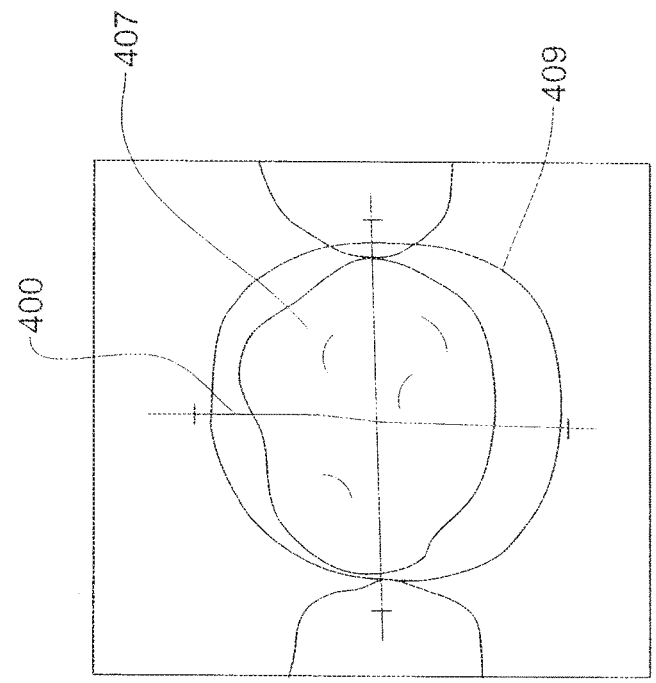
FIGS. 9a and 9b illustrate examples of display output using the system of FIG. 2 according to another embodiment.
Figure 9A:
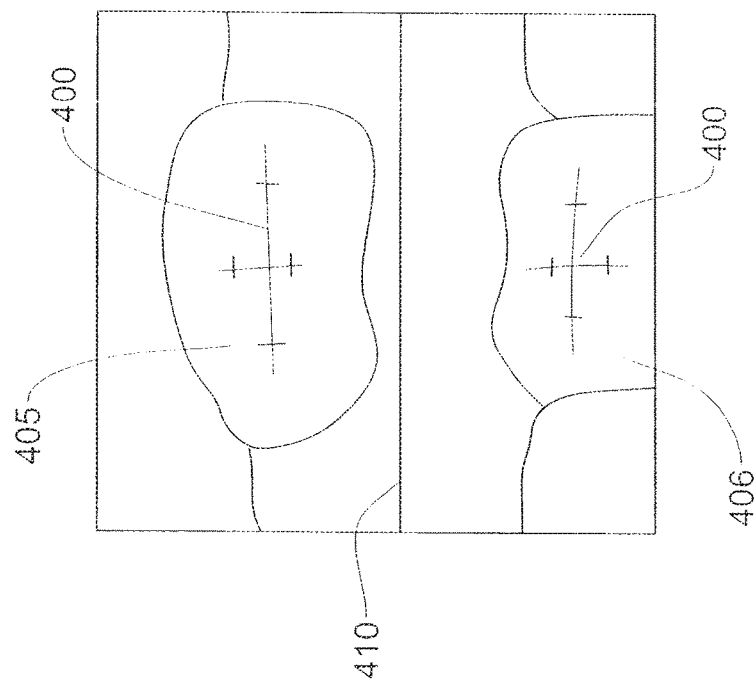

A second embodiment of step 130 is illustrated in FIGS. 9a and 9b, and in this embodiment, use is made of the video image capturing capabilities of the scanner 250, which is configured with such capabilities, for guiding the same. A suitable symbol, such as cross-hairs 400, occlusal line 410, and so on may be superimposed on the viewfinder of the scanner 250, typically displayed on the screen 220 (or printed for example). In this embodiment, the spatial relationships of step 120 are displayed from the vantage point of the scanner 250, and takes the form of providing a reference marker, such as the aforesaid cross-hairs 400, for example, on the screen where a particular part of the dental surface (e.g., the centre of a tooth viewed in the particular direction of the scanning axis) being viewed should be centred. For example, in FIG. 9a, the appropriate scan for the scanning station may be taken when the upper tooth 405 and the lower tooth 406 (previously identified by the system as being the subject of the scan) as imaged from a buccal direction by the scanner are each centralised with respect to the upper and lower cross-hairs 400. Similarly, in FIG. 9b, the tooth 407 being imaged from above is centralised with respect to cross-hairs 400. The cross-hairs may further comprise a ring 401 which further facilitates centering the tooth 407 as viewed via the scanner 250 with respect to the cross-hairs 400.

Figure 10A:
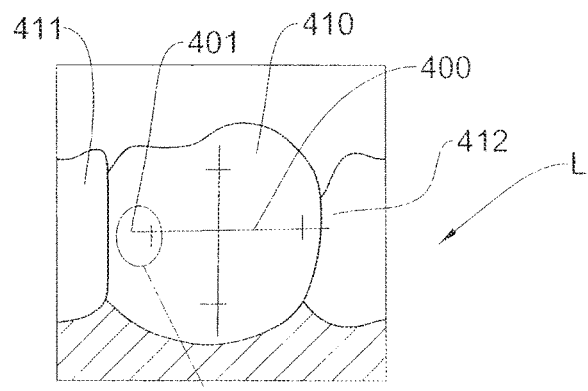
FIGS. 10a, 10b, 10c illustrate the embodiment of FIGS. 9a, 9b, used for guiding scanning from one scanning station to a next scanning station.
Figure 10B:
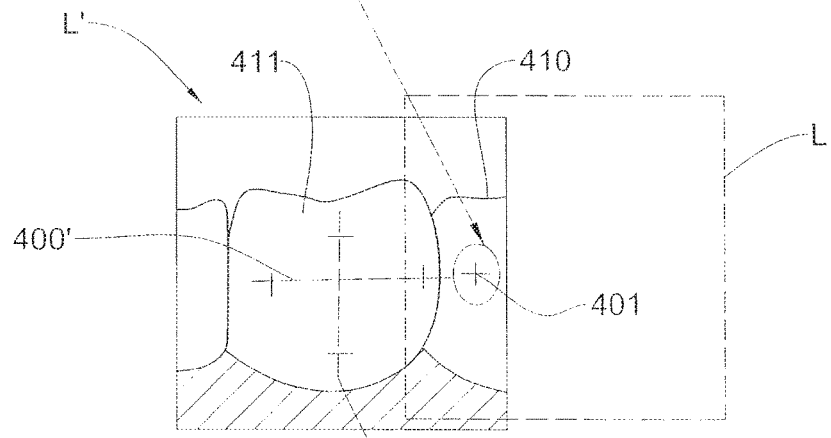
Figure 10C:
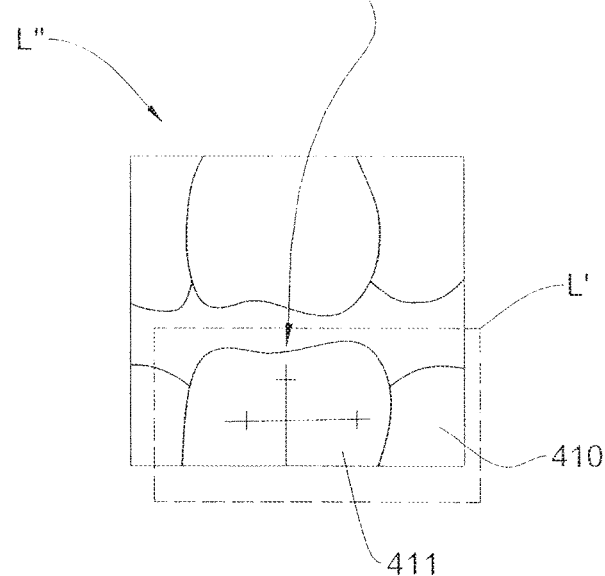

Proceeding to and identifying the next scanning station is facilitated by displacing the cross-hairs 400 to a position on the screen where the last position of the cross-hairs 400 appears in the next (now current) position of the scanning station. This is accomplished automatically by the processing unit 230 when the user is satisfied that the previous scan was properly taken, for example as described earlier in connection with the embodiment of FIGS. 8a, 8b, mutatis mutandis. The scanner is then moved so that the cross-hairs 400 (still associated in virtual space with the previous scanning station, and now appearing at the relocated position on the viewfinder) is again centralised with the previous dental surface, which has been effectively displaced from the central position of the screen to a position once again associated with the now-displaced cross-hairs 400. This automatically aligns the scanner with the next scanning station. For example, referring to FIGS. 10a to 10c, FIG. 10a illustrates an image L in buccal view of a series of teeth, with the cross-hairs 400 centralised over one particular tooth 410, the adjacent teeth 411 and 412 being partially visible. When the user is satisfied that a suitable scan was taken at this scanning station, this is made known to the system 200 in any suitable manner, and the cross-hairs 400 is moved from the previous position at the centre of the screen to the right, such that only the left hand portion 401 of the cross-hairs 400 is now visible. The user then moves the scanner such as to renew the relative position of tooth 410 with respect to cross-hairs 400 in the viewfinder, to for example as illustrated in the image of FIG. 10b, which now brings the next dental surface to be scanned, in this case tooth 411, into the main part of the viewfinder to provide image L'. The relative position of the elements in the previous image L is shown as a dotted box. When this is accomplished to the satisfaction of the user, the old position of the cross-hairs 400 is removed from the screen, and repositioned at the centre of the screen, as shown at the dotted lines 400'. A scan can now be performed at this position, which corresponds to a scanning station. To move to the next scanning station illustrated in FIG. 10c, the new position of the cross-hairs 400 is relocated, for example to the lower part of the viewfinder, and the user correspondingly translates the scanner so as to re-locate tooth 411 to maintain the previous relative position with respect to the cross-hairs 400, providing image L", and the position of the previous image L' is shown in the dotted box in this figure. This process is repeated until all the scanning stations have been passed. It may be necessary to change to direction of the scanning entirely, for example from buccal (FIG. 9a) to upper (FIG. 9b), and this can be done by guiding the user to a particular tooth where the transition is required, and then for example changing the form of the reference marker—for example, from the "+"

indicia to one also including a circle 409 (e.g. as illustrated in FIG. 9b)—signifying that an upper view should now be taken of the current tooth (or preparation or whatever dental surface is being considered). Additionally or alternatively, written, or graphic prompts may be provided in the screen, or vocal or other audio prompts provide via a speaker (not shown) urging the user to change position, and/or to move to a different dental site, specified according to the next scanning station.

Figure 11A:
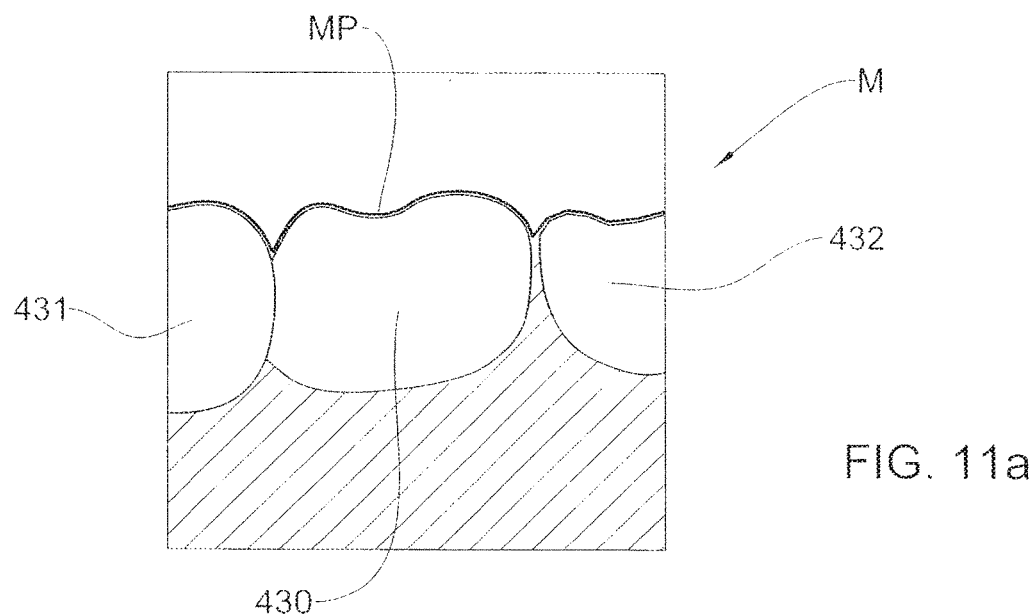
FIGS. 11a and 11b illustrate examples of display output according to a variation of the embodiment of FIGS. 9a, 9b.
Figure 11B:
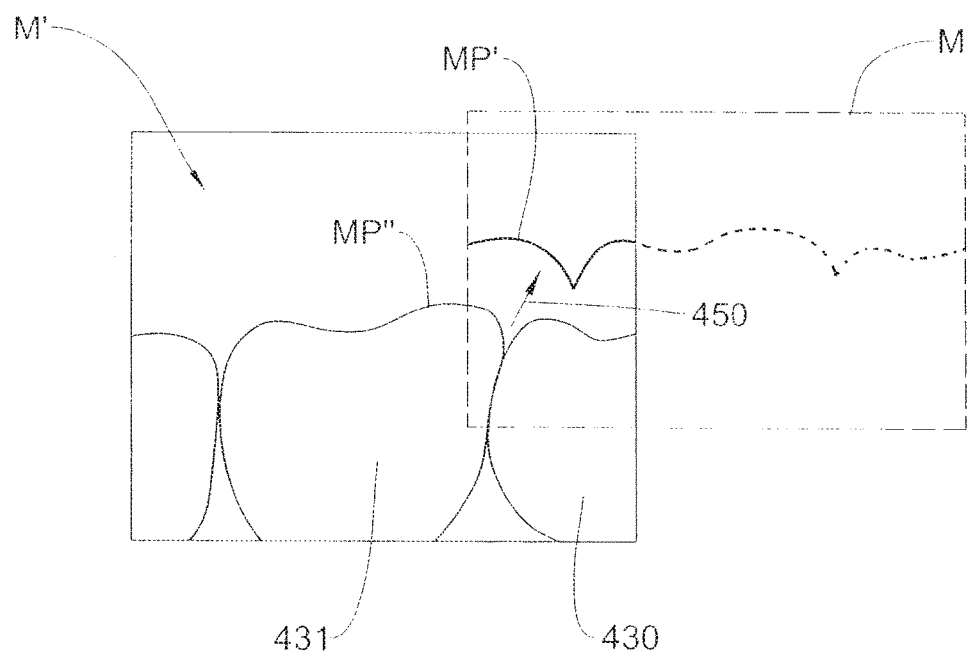

In a variation of the second embodiment of steps 130 and 140 described above, optical recognition (also known as image recognition) methods may be employed for identifying features of the dental surface being scanned at the current scanning station for guiding the user to the next scanning station. For example, and referring to FIGS. 11a and 11b, image M is a video image corresponding to the latest scan, obtained at the current scanning station. Image M shows the relative positions of various dental surfaces such as a tooth 430 in lingual view, flanked by adjacent teeth 431, 432. Suitable optical or image recognition means are applied to image M, which is first isolated in processing unit 230 by means of a suitable frame grabber, and a profile of interest, MP, is determined. Such a profile MP typically comprises an external edge of one or more of teeth 430, 431, 432 as seen from the vantage point of scanner 250, and thus typically comprises a fictitious line separating two zones that are optically different—the teeth and the background, for example. The profile MP is then reproduced as an image in the viewfinder in its original relative position in image M. Then the processing unit 230 calculates the movement of the scanner required to move to the next scanning station, and applies this movement, in a virtual manner to the profile MP, repositioning the profile MP to position MP', or at last a part thereof, in the viewfinder, as illustrated in FIG. 11b. (This is how the new position of cross-hairs 400 described above may in practice be calculated as well, for example.) The user then moves the scanner 250, mimicking the virtual movement previously calculated, until the image seen by the viewfinder is brought into alignment with the repositioned profile MP'. FIG. 11b shows image M' obtained prior to full alignment—the scanner 250 having to be moved in the direction of arrow 450 until the profile MP' is superposed on part of the edges MP'' of the teeth as seen via the viewfinder.

The guiding of the dental practitioner between the different scanning stations has been described above in graphical terms. Optionally or alternatively, the guiding may take any suitable form. For example, oral commands may be provided, asking the practitioner to now move the scanner to the left 3 mm and upwards 2 mm, for example, using any suitable speech software operating on scanning station data inputs provided by the processing unit 230. Alternatively, non-oral audio commands may be provided, for example coded bells or beeps, the pattern and intensity thereof being capable of being interpreted by the user in terms of the required movement in a number of directions, for example.

Additionally or alternatively, non-graphical means may be used for guiding the user between scanning stations. For example, suitable LED's may be provided in the viewfinder, or images of arrows, for example, for guiding the user in the required directions to the next scanning station.

Advantageously, the scanner 250 comprises an inertial system or a suitable tracking system, that is capable of determining a change of position and/or orientation thereof relative to a datum position/orientation. Thus, the actual position/orientation of the scanner 250 can be checked automatically against the desired position for the next scan, and any suitable means—audio and/or visual for example—may be used for guiding the user to the correct position based on the difference between the current position and the desired position. For example, a beep may be sounded the frequency of which increases the closer the scanner 250 is to the desired position. Optionally, a second inertial or tracking system may be coupled to the head or jaws of the patient, so that any movement thereof may be compensated for.

Optionally, a series of indicia may be provided, each indicia in the series corresponding to a different scanning station. The series of indicia may be displayed m a predetermined sequence, a next indicia being displayed after the intraoral cavity has been scanned at the previous scanning station with its corresponding indicia. Optionally, the next indicia may be displayed together with the current, i.e., the immediately preceding indicia. The indicia relating to different said parameters are displayed in different colors one from another. Thus, these indicia help to identify which scanning station the user is at, and which is the next station, for example. The indicia may comprise a series of numbers (for example "1/4", "2/4", "3/4", "4/4") or symbols, for example.

In another aspect of the present invention, a computer readable medium is provided that embodies in a tangible manner a program executable for guiding the scanning of the intraoral cavity of a patient. The computer readable medium comprises:

(a) a first set of data representative of target parts of the intraoral cavity that it is desired to have scanned;

(b) a second set of data representative of spatial relationships between a scanning device and said target parts of the intraoral cavity suitable for enabling said target parts to be scanned by said scanning device;

(c) means for displaying said second data.

The medium may comprise, for example, optical discs, magnetic discs, magnetic tapes, and so on.

According to some aspects of the invention, a method and system are provided for scanning, and for facilitating scanning of, an intraoral cavity. The target parts of the intraoral cavity that it is desired to have scanned are identified, and the spatial relationships between a scanning device and the target parts of the intraoral cavity suitable for enabling said target parts to be scanned by said scanning device, are also identified or otherwise determined. These relationships are then displayed, and the displayed relationships are used as a guide for scanning the intraoral cavity.

In the method claims that follow, alphanumeric characters and Roman numerals used to designate claim steps are provided for convenience only and do not imply any particular order of performing the steps.

Finally, It should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. A method for providing scanning guidance for a scanning device, comprising:
   (a) receiving, at a computer system, user input selecting target parts of an intraoral cavity to be subsequently scanned by said scanning device;
   (b) determining, using the computer system, spatial relationships between the scanning device and said target parts of the intraoral cavity suitable for enabling said target parts to be subsequently scanned by said scanning device, wherein visual guide instructions for positioning and orienting said scanning device are generated by the computer system based on said spatial relationships; and (c) displaying, with the computer system on a display, said visual guide instructions for positioning and orienting said scanning device relative to the intraoral cavity in a manner substantially conforming to said spatial relationships;

wherein said visual guide instructions comprise a symbol representative of a profile corresponding to an expected view of said target parts or of ancillary parts in said intraoral cavity associated with said target parts, the expected view corresponding to the determined spatial relationships, and the symbol comprising a line defining an interface between a plurality of image zones.

2. The method according to claim 1, wherein said scanning device provides 3D data of said target parts for use in a predetermined dental procedure.

3. The method according to claim 2, wherein said step (a) includes receiving user input identifying said ancillary parts in said intraoral cavity associated with said target parts, wherein 3D data of said ancillary parts is also provided for use in said predetermined dental procedure;

said step (b) comprises, for each said target part and each said ancillary part, determining for said scanning device a series of spatial parameters, each comprising scanning station data for enabling said scanning device to fully scan said corresponding target part or ancillary part;

wherein said scanning station data of said series of spatial parameters includes a proximity and a relative orientation of said scanning device with respect to said target part or ancillary part such as to enable said scanning device to obtain 3D topographical data of an area of said target part or ancillary part;

wherein said series provides 3D topographical data for a corresponding plurality of said areas, wherein said spatial parameters of said series are determined such that at least some adjacent said areas overlap one another.

4. The method according to claim 3, wherein step (c) comprises displaying a nominal image comprising an image of at least a portion of a nominal intraoral cavity comprising corresponding said target parts and said ancillary parts, and an image of a nominal scanning device, wherein the nominal intraoral cavity and the image of the nominal scanning device are displayed in a spatial relationship with respect to one another corresponding to the spatial relationship as determined in step (b) for at least one spatial parameter of said series of spatial parameters.

5. The method according to claim 4, wherein a series of said nominal images are provided, each image in said series corresponding to a different one of said spatial parameters of said series of spatial parameters.

6. The method according to claim 5, wherein said series of nominal images is displayed in a predetermined sequence.

7. The method according to claim 4, wherein said nominal image comprises 3D attributes, and wherein said nominal image comprises said nominal intraoral cavity at any desired orientation with respect to a predetermined coordinate system.

8. The method according to claim 7, wherein said orientation corresponds to a real life view of the intraoral cavity of a patient from the vantage point of a dental practitioner.

9. The method according to claim 3, wherein step (c) comprises displaying indicia on a viewfinder capable of providing a video image of a field of view of said scanning device, said indicia being indicative of a desired position for associating a predetermined portion of said target parts or ancillary parts in a particular manner with respect therewith.

10. The method according to claim 9, wherein said expected view comprises a view from said viewfinder.

11. The method according to claim 10, wherein optical recognition methods are applied to said video image for providing a profile of the image, said symbol comprising said profile.

12. The method according to claim 11, wherein said profile comprises a shaped line shaped as an outline of a tooth as seen by said viewfinder.

13. The method according to claim 10, wherein said symbol comprises a shaped line shaped as an outline of a tooth seen in any one of a top view, buccal view or lingual view.

14. The method according to claim 3, wherein said procedure comprises a prosthodontic procedure for a crown with respect to a preparation, said target parts comprising said preparation, and said ancillary parts comprising at least a portion of the teeth adjacent to said preparation and facing said preparation from the opposed jaw.

15. The method according to claim 3, wherein said procedure comprises a prosthodontic procedure for a bridge with respect to a plurality of preparations, said target parts comprising said plurality of preparations, and said ancillary parts comprising at least a portion of the teeth adjacent to a furthermost distal preparation and adjacent a furthermost mesial preparation, and at least a portion of the teeth facing said plurality of preparations from the opposed jaw.

16. The method according to claim 2, wherein said procedure comprises an orthodontic procedure, and said target parts comprise the full dentition of at least one jaw of said intraoral cavity.

17. A system for scanning of an intraoral cavity, the system comprising:

a scanning device;

an input module configured to receive a user input selecting target parts of the intraoral cavity to be subsequently scanned by said scanning device;

a processing module configured to determine spatial relationships between the scanning device and said target parts of the intraoral cavity suitable for enabling said target parts to be subsequently scanned by said scanning device and to generate, based on said spatial relationships, visual guide instructions for positioning and orienting said scanning device relative to the intraoral cavity in a manner substantially conforming to said spatial relationships; and a display module comprising a display configured to display said spatial relationships so as to provide a visual guide protocol for a user to position and orient said scanning device relative to the intraoral cavity in a manner substantially conforming to said spatial relationships during scanning of said intraoral cavity, thereby providing guidance for subsequent scanning of said target parts by said scanning device; and wherein said visual guide instructions comprise a symbol representative of a profile corresponding to an expected view of said target parts or of ancillary parts in said intraoral cavity associated with said target parts, the expected view corresponding to the determined spatial relationships, and the symbol comprising a line defining an interface between a plurality of image zones.

18. The system according to claim 17, wherein said scanning device is configured for scanning according to said spatial relationships.

19. The system according to claim 18, wherein said scanning device comprises a probe for scanning according to said spatial relationships.

20. The system according to claim 17, wherein said scanning device is configured to provide 3D data of said target parts for use in a predetermined dental procedure.

* * * * *